United States Patent [19]

Goble

[11] 4,258,715
[45] Mar. 31, 1981

[54] RADIATION CROSSLINKED ACRYLAMIDE POLYMER COMPOSITIONS AND SHAPED ARTICLES THEREFROM

[75] Inventor: Paul H. Goble, Painesville, Ohio

[73] Assignee: Diamond Shamrock Corporation, Dallas, Tex.

[21] Appl. No.: 967,606

[22] Filed: Dec. 8, 1978

[51] Int. Cl.³ .............................................. A61F 5/44
[52] U.S. Cl. ............................ 128/283; 260/33.4 R; 526/230
[58] Field of Search ............................... 128/155–156, 128/260–262, 283; 526/230, 317, 320, 323; 260/33.4 R

[56] References Cited

U.S. PATENT DOCUMENTS

| | | | |
|---|---|---|---|
| 3,475,363 | 10/1969 | Gander | 128/156 |
| 3,810,468 | 5/1974 | Harper et al. | 128/156 |
| 3,877,431 | 4/1975 | Kross | 128/283 |
| 3,963,685 | 6/1976 | Abrahams | 128/156 |
| 3,980,084 | 9/1976 | Kross | 128/283 |
| 3,983,297 | 9/1976 | Ono et al. | 128/156 |
| 4,074,039 | 2/1978 | Lim et al. | 128/156 |
| 4,078,568 | 3/1978 | Estes et al. | 128/283 |
| 4,153,055 | 5/1979 | Etes | 128/283 |
| 4,192,727 | 3/1980 | Ward | 128/287 |

Primary Examiner—Robert W. Michell
Assistant Examiner—C. F. Rosenbaum
Attorney, Agent, or Firm—Stuart L. Melton

[57] ABSTRACT

Improved shaped polymeric articles, including ostomy seals, are obtained by radiation crosslinking an acrylamide polymer composition comprising a water-soluble acrylamide polymer plasticized with a quantity of a water-miscible polyol (containing water) that provides a soft, flexible and elastomeric composition.

8 Claims, 2 Drawing Figures

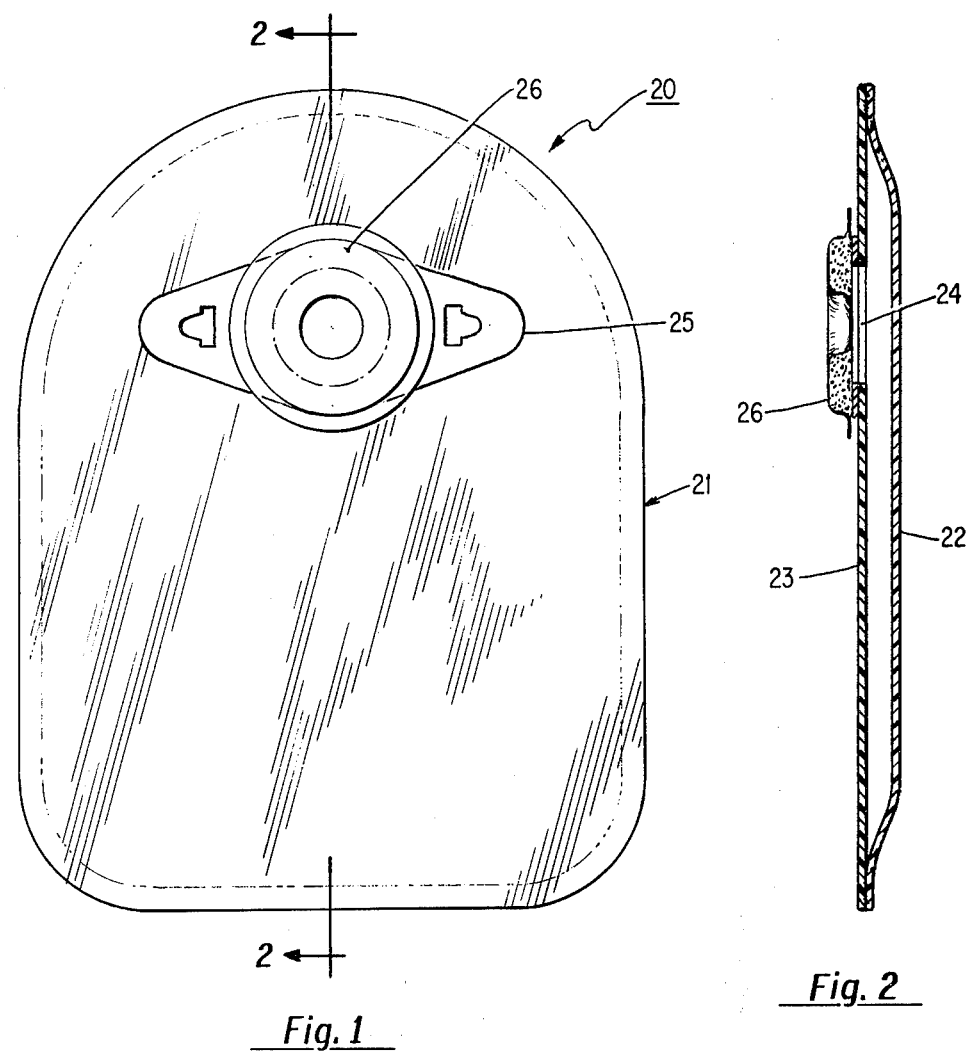

RADIATION CROSSLINKED ACRYLAMIDE POLYMER COMPOSITIONS AND SHAPED ARTICLES THEREFROM

BACKGROUND OF THE INVENTION

This invention relates to improved sealing means for ostomy appliances. More particularly, it is directed to ostomy sealing means (hereinafter called "ostomy seals") made from particular crosslinked compositions having a good balance of physical properties and improved resistance to degradation in service.

The term "Ostomy" has come into use to define, in a broad sense, the surgical procedures known as colostomy ileostomy, cecostomy, ureterostomy, ileal conduit, ileal bladder, wet colostomy, etc. This surgery usually results in an artificial opening through the abdominal wall for the terminal end of the intestine or a duct, called a stoma to discharge the body wastes of feces or urine.

Many ostomy devices or appliances have been developed through the years to aid the ostomy patient. Typical of such devices are ostomy bags or pouches constructed of flexible plastic or rubber materials, for receiving and holding these body wastes. In use it is necessary that a liquid-proof seal be maintained between the patient's skin and the bag (or retainer plate to which the bag may be attached) to prevent leakage of the waste material onto the skin of the patient surrounding the stoma or even therebeyond. In addition to the odor that would result from such leakage, irritation of the peristomal skin of the patient surrounding the stoma is extremely likely under circumstances of leakage, and in ileostomy cases, where the discharge is from the small intestine, ingestive liquids can actually digest the skin of the patient if they come in contact with it.

Consequently, extensive efforts have been directed to developing sealing materials and means that provide effective liquid-tight seals with minimum irritation to the peristomal skin. Ideally an ostomy seal should be soft and flexible so as to conform to the body, yet have sufficient elasticity and recovery to firmly engage the stoma. It should be non-allergenic, non-irritating and non-sensitizing; and desirably possess visual appeal and freedom from odor. Further, it should be resistant to acids, bases, enzymes and other materials which may be found in intestinal and urinary discharges. Lastly, and possibly most critical, it should be capable of absorbing moisture from the skin and from any body wastes it contacts, without disintegrating or developing a slimy surface so as to maintain useful and serviceable cohesive and adhesive properties. Of equal importance, all these properties must be provided with sealing compositions that are both economical and easily fabricated into ostomy seals, which may be in the form of pads, gaskets, rings and the like as is well-known to the art.

SUMMARY OF THE INVENTION

While a number of compositions have been developed for ostomy seals, none satisfy all the prerequisites of an ideal seal. Consequently, it is an object of this invention to provide an improved ostomy seal (and ostomy appliances utilzing such a seal) which more completely and nearly satisfies these requirements. These and still other objects and advantages, which will become apparent from the following description and claims, are attained with an ostomy seal that is made with a composition comprising a water-dispersible acrylamide polymer, solvated and plasticized with a quantity of water-miscible polyol, or mixture of polyols, containing water providing a seal that is soft, flexible and elastomeric; the composition being irradiated with ionizing radiation after it is formed into the desired seal configuration to effect substantial crosslinking.

BRIEF DESCRIPTION OF THE DRAWINGS

One embodiment of the invention is illustrated in the drawings wherein:

FIG. 1 is a front-elevational view of an ostomy appliance embodying the present invention.

FIG. 2 is a longitudinal-sectional view taken along the line 2—2 in FIG. 1.

DETAILED DESCRIPTION

Referring to the drawings, an ostomy appliance 20 of the present invention comprises a pouch receptacle 21 of flexible plastic film or sheet material with spaced apart front and back walls 22 and 23 sealed at their edges and including, in one wall thereof, a stoma accommodating opening 24. A relatively stiff faceplate or retainer 25 with a central opening therein is affixed to the pouch wall so that the central opening is aligned with the corresponding opening in the pouch wall. The seal composition 26 of the present invention is provided in annular form and adhesively affixed to faceplate 25.

In the following description and claims, all parts and percentages are by weight.

The acrylamide polymer used in the invention ostomy seal composition is a water-dispersible acrylamide polymer or copolymer capable of forming a 1% total solids a true aqueous solution and/or a stable hydrocolloidal dispersion. It has been found that "nonionic" virtual homopolymers of acrylamide (containing no more than about 4% by weight sodium acrylate) having high molecular weight, such as Reten 420 (Hercules), give seals having, after 2.5 megarads gamma radiation, only 300% or less water swelling (as mesured by weight gain) after 24 hours water immersion and, hence, constitutes a preferred embodiment. On the other hand, copolymers containing appreciable quantities of anionic groups (such as Reten 421 and 425 containing 10% or more by weight of sodium acrylate) or cationic groups (such as Reten 210 and 220 containing 10% or more by weight of beta-methacryloyloxyethyltrimethyl ammonium methyl sulfate) give seals, after equal irradiation, swelling 2,250% (Reten 421), 3,800% (Reten 425) and 1,050% (Reten 210). Consequently, for minimum water swellability, the total weight of monomer units having anionic and/or cationic functionality in the copolymer or mixture of copolymers utilized in the invention seals preferably will not exceed about 5% of the total weight of acrylamide polymers employed; and, ideally, will not exceed about 2% of the total weight of the polymer or mixture of polymers for lowest water sensitivity. Equally satisfactory, are copolymers of a major portion of acrylamide (51–100 weight percent) and a minor portion (0–49 weight percent) of a copolymerizable vinyl monomer or monomer mixture, free of ionic groups, in a quantity not significantly diminishing the polymer's water dispersibility. Useful vinyl comonomers may be styrene, vinyl acetate, acrylonitrile, methyl ether, methyl vinyl ether, vinyl pyrolidone, beta-hydroxyl ethyl and propyl acrylates, methyl acrylate and the like, and even divinyl monomers such as divinyl benzene, methylenebisacrylamide, and N,N- dially-acrylamide, if employed in a quantity small enough (e.g., up to about 5 weight percent) not to disrupt the water dispersibility of the acrylamide polymer. Also alpha-methyl vinyl

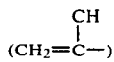

monomers (whose polymers exhibit chain scission when irradiated), such as methacrylamide, N-methyl methacrylamide, methyl methacrylate, betahydroxy ethyl and propyl methacrylates, vinylidene chloride, and the like, may be used as a copolymerizable monomer if the quantity is limited so that, when irradiated, crosslinking of the copolymer predominates over degradation. Finally, while acrylamide polymers and copolymers are preferred, water-dispersible polymers and copolymers of N-substituted acrylamide, such as N-methyl acrylamide, N-methylol acrylamide, and N-isopropyl acrylamide may also be used. Hence, in the following description and in the claims, it should be understood that the expression "acrylamide polymer" is used in the generic sense to encompass not only the virtual homopolymer of acrylamide, but also water-dispersible copolymers of acrylamide and water-dispersible polymers and copolymers of N-substituted acrylamide, which are capable of cross-linking when exposed to ionizing radiation, as well as mixtures of any of these polymers. The molecular weight of the acrylamide polymer should be high enough so as to give an ostomy seal having, after radiation crosslinking, substantially elastomeric-like properties. Typically, useful polymers have given 1% aqueous solutions (or gels) at 25° C. having a Brookfield viscosity of about 10 centipoises or more, nd a range of particle sizes such that virtually none is retained on a No. 20 U.S. mesh screen, while about 90–100% is retained on a No. 100 U.S. mesh screen. Polymers having smaller particle-sizes may be used, but will gel faster and, hence, may require a compensating reduction in the water level of the polyol(s) and/or temperture of gellation. Because of this, they may be preferred when only a small amount of water, e.g., 1 to 2%, is used in the solvating polyol(s).

The water-miscible polyol, or mixture of polyols, containing water that is used to solvate and plasticize the acrylamide polymer is chosen to provide a seal composition that is soft, flexible and elastomeric and has no tactile surface exudation of polyol after gellation and radiation crosslinking. Because of its excellent solvating properties and low toxicity and absorption into the skin, glycerine is the preferred polyol. It may be used either by itself or combined with other water-miscible polyols—either of the primary (solvating) or secondary (diluting) type. Other suitable solvating polyols include ethylene glycol, diethylene glycol, and sorbitol (when it is used with sufficient water and/or other polyols to provide a liquid mixture). Useful secondary water-miscible polyols include, without limitation, propylene glycol, dipropylene glycol, the butylene glycols, and polyethylene glycols (above diethylene glycol) having a molecular weight of up to about 600. Typically, the plasticizer mixture will comprise about 20–99 weight percent primary polyol, about 0–79 weight percent secondary polyol and about 1–20 weight percent water. The preferred level of water will vary depending on the type of primary polyol and percentage of secondary polyol used. For example, ethylene glycol and/or glycerine, alone, give excellent results with as little as 1% water, although 3–7 percent is typically used to accelerate gellation. Diethylene glycol, on the other hand, requires more water, typically 5–15 weight percent, for good solvating properties. Higher quantities of secondary polyol, as for example 20% or more, also necessitate the use of higher water levels, such as 5% to 15% if suitably rapid gellation is to be attained. Additionally, temperature affects the minimum level of water required: more being required when lower gelling temperatures are used. Finally, acrylamide polymes of higher molecular weight and/or less hydrophilic nature may require more water in the polyol plasticizer. In work to date, the best balance of seal properties coupled with good processing and gelling characteristics have been obtained with polyol plasticizer mixtures comprising about 50–99 percent glycerine, 0–49 percent secondary polyol, and 1–18 percent water. In the above discussion, the percent water includes, of course, not only water added to the polyol, but also that present in the polyol as purchased.

The quantity of polyol, or mixtures of polyols, containing water used is sufficient to provide a seal that is, as previously stated, soft and flexible and yet elastomeric. Illustrative of seal physical properties obtained are: Shore A, 1–5 (or Sponge Rubber Gauge values, 80–95); tensile strength at break, 16–22 psi; tensile modules 12–30 psi; elongation at break 350–600 percent; crescent tear, 5–7 psi; and, compression modulus, 15–35 psi. Typically, about 125 to 200 parts of polyol(s) containing water per 100 parts of acrylamide polymer provides such properties, with about 150–175 parts being the generally preferred range.

The ostomy seal is typically made by blending the particulate acrylamide polymer or polymers and any solid adjuvant (pigment, colorant, antiseptic, stabilizer and the like) being used, and admixing this blend with the polyol, or mixture of polyols, containing water to form a homogeneous admixture. When adjuvants soluble in the glycols and/or water are used, they may be be predispersed in the glycol(s)-water mixture. Also, at times, it may be advantageous to prewet and predisperse the polymer and/or solid adjuvants with some or all of the polyol(s) before admixing the water. These and still other techniques of combining and mixing the seal ingredients are familiar and known to those skilled in the art.

After all the ingredients are well dispersed, the resulting liquid composition is formed into the desired seal configuration, such as ring, pad, gasket and the like, by casting the composition into an appropriate mold and allowing it to gel. If desired, two or more layers of different compositions may be successively cast, or be combined after gelling, to provide a seal having optimum properties for each face. The time required for gellation will vary depending upon the seal composition—particularly the water level—and temperature. Typically, one or both are set—the rate of gellation increasing as the water level and/or temperature increase—to effect incipient gellation within 5–60 minutes. The ostomy seal is then aged for a period and at a temperature sufficient to ensure that virtually all the acrylamide polymer is solvated and gelled prior to the seal being irradiated, the minimum time again being dictated by the level of water and temperature. Typically, seals have been aged six days at ambient temperature (about 25° C.) to ensure substantially complete gellation. Shorter or longer times may be used. To shorten aging, elevated temperatures, e.g., 40°-90° C., may be used so long as no appreciable water is lost from the seals. If necessary, excessive water loss may be prevented by means such as aging the seals in a high humidity environment or covering the seals with a moisture barrier.

After aging, the ostomy seal is irradiated with an ionizing radiation to effect crosslinking, typically, at ambient conditions and temperature (air and 20°-35° C.). Usually, radiation doses of at least about 0.7 megarads (Mrads) are required to provide sufficient crosslinking to render the seal usefully resistant to moisture degradation, which can manifest itself as excessive swelling with a concomitant loss of useful physical properties, and/or slimy surfaces that can cause loss of seal adhesion to the skin and/or ostomy bag. For best results from a cost-performance standpoint, radiation levels of about 1.4 to 2.1 Mrads are used to minimize water sensitivity. Higher doses may be used, but with little gain compared to their higher costs. While any high energy particulate or electromagnetic radiation, such as accelerated electrons, protons, neutrons, x-rays, gamma rays and the like, theoretically may be used, gamma radiation is preferred from a cost-efficiency standpoint. Suitable gamma-ray sources include cesium-137 and cobalt-60. Alternatively, the minimum radiation required for effective crosslinking may be measured by the swellability of the irradiated seal in water: adequate irradiation giving seals increasing in weight no more than about 400% after 24 hours immersion in water at 25° C., and preferably no more than about 300%.

In some instances, irradiation will cause the seal to develop a slight odor when stored in gas-impermeable containers, which odor dissipates when the seals are exposed to air. It has been found that this odor can be virtually prevented, if deemed objectionable, by incorporating a water-soluble, reducing-agent stabilizer into the seal composition. Sodium meta-bisulfite ($Na_2S_2O_5$) has been found to be especially effective at a level of 0.3 to 0.6 parts per 100 parts of the acrylamide polymer depending upon the radiation dose utilized: higher doses requiring larger amounts of the stabilizer. Other potentially useful stabilizers include sodium bisulfite ($NaHSO_3$), sodium thiosulfate ($Na_2S_2O_3.5H_2O$), hydroquinone and the like, which at the effective concentration utilized should not appreciably diminish crosslinking of the acrylamide polymer.

Other ingredients may be incorporated into the invention seals, care being taken to choose adjuvants and quantities that are compatible with the seal composition and do not appreciably diminish its desirable physical and chemical properties or significantly inhibit its radiation crosslinking. Examples of other ingredients that may be used are: other types of water-soluble polymers both natural and synthetic, such as cornstarch, gelatin, casein, guar gum, carboxy methyl cellulose, high-molecular-weight polyethylene oxide, polyvinyl alcohol, vinyl acetate-maleic halfamide copolymers; antiseptic agents; bactericides; fungicides; polyvalent metal (Ca, Mg, etc.) hydroxides and salts; crosslinking agents, such as methylene bisacrylamide; pigments; dyes; fillers; pH-buffers; tackifiers; deodorants; and the like.

When the seal composition is deficient in tackiness or adhesiveness to the skin and/or the ostomy bag, a suitable adhesive may be applied to one or both faces of the seal by means well-known to the art. For example, the surface of the seal, after being gelled and either before or after irradiation, may be coated with a suitable liquid adhesive, which is then dried or polymerized to the solid state. Alternatively, the adhesive layer may be preformed on a release sheet, and the ostomy seal either cast (before gellation) or laminated (after gellation, and either before or after irradiation) to the adhesive layer. Illustrative of adhesives that have been used are Swift No. 45508 polyvinyl acetate/polyacrylate adhesive, Dow Corning No. 355 medical-grade adhesive, and 3M's ST-1524 transfer tape.

EXAMPLES 1–8

Eight ostomy rings (about one-quarter inch thick) were made with Reten 420 (acrylamide homopolymer containing not more than 4% sodium acrylate and having a Brookfield viscosity at 1% total solids in water at 25° C. of about 300 cps or more) plasticized with: a glycerine-propylene glycol mixture containing 6.77% water (examples 1–6), or just glycerine containing 7% water (examples 7 and 8). All the rings were conditioned seven days at ambient conditions (air at 25°-28° C.) before being irradiated, also at ambient conditions, with gamma radiation (except example 1, the control) at the doses indicated in the Table. Eleven days after being made, two-gram sections of the rings were immersed in water at ambient temperature (about 25° C.) and the increase in weight and gel strength measured after 4, 8, 24 and 72 hours immersion. The data in the Table indicates that acceptable water swelling and gel strength are achieved with as little as 0.72 megarads irradiation, and that nearly maximum water resistance is achieved with 2.16 megarads; little additional water resistance being imparted at higher radiation levels. Examples 7 and 8 show that nearly identical properties are obtained when glycerine is used as the only polyol. Surprisingly, the radiation had little effect on the other physical properties, which were, both before and after irradiation, within the ranges hereinbefore delineated in connection with the level of polyol typically employed. Also, when an adhesive is employed, such as the 3M transfer adhesive, it also appeared to be uneffected by the radiation levels utilized.

| | Effect of Radiation on Water Sensitivity and Gel Strength | | | | | | | |
|---|---|---|---|---|---|---|---|---|
| Example | 1 | 2 | 3 | 4 | 5 | 6 | 7 | 8 |
| Reten 420 | 100 | 100 | 100 | 100 | 100 | 100 | 100 | 100 |
| glycerine (anhydrous) | 143.7 | 143.7 | 143.7 | 143.7 | 143.7 | 143.7 | 160 | 160 |
| propylene glycol | 16.6 | 16.6 | 16.6 | 16.6 | 16.6 | 16.6 | — | — |
| distilled water | 11.3 | 11.3 | 11.3 | 11.3 | 11.3 | 11.3 | 12 | 12 |
| Radiation exposure (Mrads) | 0.00 | 0.36 | 0.72 | 1.44 | 2.16 | 5.76 | 1.44 | 2.16 |
| Weight gain (in percent) after immersion in water for: | | | | | | | | |
| 4 hours | 185 | 165 | 160 | 140 | 145 | 125 | — | — |
| 8 hours | 250 | 250 | 220 | 180 | 190 | 175 | 180 | 175 |

-continued

| Example | Effect of Radiation on Water Sensitivity and Gel Strength | | | | | | | |
|---|---|---|---|---|---|---|---|---|
| | 1 | 2 | 3 | 4 | 5 | 6 | 7 | 8 |
| 24 hours | N.M.[1] | 410 | 360 | 295 | 280 | 250 | 290 | 265 |
| 72 hours | — | N.M.[1] | 530 | 410 | 360 | 305 | 410 | 350 |
| Gel strength[2] after immersion in water for: | | | | | | | | |
| 8 hours | — | + | | | | | | |
| 24 hours | | — | + | | | | | |
| 72 hours | | | — | + | + | + | + | + |

[1] N.M. = not measurable: sample swelled so much that it could not be handled and weighed.
[2] Gel strength measured by centering a 750 gram, 1.9 cm diameter bar upon the center of the water-swollen ring section. A strong ring supports the bar for 30 seconds (denoted by "+"), while a weak ring does not (denoted by "−").

What is claimed is:

1. A shaped polymeric product suitable for application to human skin comprising a water-dispersible acrylamide polymer solvated and plasticized with a water-miscible polyol, or mixture of polyols, containing water wherein the quantity of polyol(s) containing water is between about 125–200 parts per 100 parts of said acrylamide polymer providing a polymeric product that is soft, flexible and elastomeric, said polymeric product being irradiated with ionizing radiation to effect substantial crosslinking of the acrylamide polymer thereby rendering it substantially insoluble in water.

2. The shaped polymeric product of claim 1 wherein the polyol comprises at least 50 percent glycerine and one percent water, and the seal is irradiated with at least 0.7 megarads of gamma radiation.

3. The shaped polymeric product of claim 2 wherein the acrylamide polymer is a copolymer containing at least 51 percent acrylamide.

4. The shaped polymeric product of claim 2 wherein a mixture of acrylamide polymers is used, and at least 50 percent of the mixture is a virtual homopolymer of acrylamide.

5. The shaped polymeric product of claim 2 wherein the acrylamide polymer is virtually only polyacrylamide.

6. The shaped polymeric product of claims 1, 2, 3, 4 or 5 which further includes a stabilizer reducing odor caused by irradiation.

7. In an ostomy drainage device, the improvement comprising employing the shaped polymeric product of claim 6 as a seal for said ostomy drainage device.

8. In an ostomy drainage device, the improvement comprising employing the shaped polymeric product of claims 1, 2, 3, 4 or 5 as a seal for said ostomy drainage device.

* * * * *